(12) United States Patent
Tsai et al.

(10) Patent No.: US 9,700,397 B2
(45) Date of Patent: Jul. 11, 2017

(54) IMPLANT CARRIER, MIXING POT, AND IMPLANT CARRIER ASSEMBLY

(71) Applicant: Metal Industries Research & Development Centre, Kaohsiung (TW)

(72) Inventors: Tung-Lin Tsai, Tainan (TW); I-Wen Huang, Kaohsiung (TW); Bo-Wei Pan, Kaohsiung (TW); Hsien-Ju Wu, Kaohsiung (TW); Pei-Hua Wang, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 0 days.

(21) Appl. No.: 14/954,917

(22) Filed: Nov. 30, 2015

(65) Prior Publication Data

US 2017/0151050 A1     Jun. 1, 2017

(51) Int. Cl.
| A61F 2/00 | (2006.01) |
| B65D 81/22 | (2006.01) |
| B65D 81/32 | (2006.01) |
| B65D 43/02 | (2006.01) |

(52) U.S. Cl.
CPC ............ *A61F 2/0095* (2013.01); *B65D 43/02* (2013.01); *B65D 81/22* (2013.01); *B65D 81/3216* (2013.01)

(58) Field of Classification Search
CPC  A61B 17/06; A61B 19/02; A61C 8/00; A61F 2/0095; B65D 25/08; B65D 43/02; B65D 81/22; B65D 81/32; B65D 81/3216
USPC .............. 206/63.3, 63.5, 219–222, 438–441, 206/570–572; 366/130; 433/77, 172–175
See application file for complete search history.

(56) References Cited

U.S. PATENT DOCUMENTS

| 2,395,221 A | 2/1946 | Hampel |
| 3,462,034 A | 8/1969 | Friedberg |
| 3,762,540 A * | 10/1973 | Baumann ............... A61C 5/066 206/219 |
| 3,890,204 A | 6/1975 | Avery |
| 3,904,058 A | 9/1975 | Rosenstein |
| 3,981,398 A | 9/1976 | Boshoff |

(Continued)

FOREIGN PATENT DOCUMENTS

| CN | 102056566 | 5/2011 |
| EP | 0669111 | 8/1995 |

(Continued)

OTHER PUBLICATIONS

"Office Action of Taiwan Counterpart Application", issued on Oct. 24 1, 2016, p. 1-p. 6.

*Primary Examiner* — Bryon Gehman
(74) *Attorney, Agent, or Firm* — Jianq Chyun IP Office

(57) ABSTRACT

An implant carrier assembly, including a first housing, a second housing, a mixing pot for receiving powder, and a sealed container for receiving liquid, is provided. The first housing and the second housing are detachably assembled to each other to form a receiving space. An implant is received therein or removed therefrom. The second housing has a hole communicating with the receiving space. The sealed container is inserted into the mixing pot, and the mixing pot is assembled to the second housing, such that the sealed container is packed and squeezed inside the mixing pot and broken and the liquid flows out of the sealed container. The powder and the liquid are mixed and flow into the receiving space through the hole.

17 Claims, 5 Drawing Sheets

(56) References Cited

U.S. PATENT DOCUMENTS

| | | | |
|---|---|---|---|
| 4,027,392 A | 6/1977 | Sawyer et al. | |
| 4,364,473 A | 12/1982 | Bogaert | |
| 4,615,462 A | 10/1986 | Sacherer et al. | |
| 4,666,037 A | 5/1987 | Weissman | |
| 4,856,648 A | 8/1989 | Krueger | |
| 5,393,497 A * | 2/1995 | Haber | A61J 1/2089 |
| | | | 206/219 |
| 5,961,330 A | 10/1999 | Hanson | |
| 6,261,097 B1 | 7/2001 | Schmutz et al. | |
| 6,280,192 B1 | 8/2001 | Groll et al. | |
| 6,386,872 B1 * | 5/2002 | Mukasa | A61C 5/064 |
| | | | 206/219 |
| 6,454,567 B1 | 9/2002 | Carchidi et al. | |
| 6,543,612 B2 * | 4/2003 | Lee | B65D 81/3222 |
| | | | 206/222 |
| 6,827,575 B1 | 12/2004 | Jorneus | |
| 6,913,465 B2 | 7/2005 | Howlett et al. | |
| 6,951,461 B2 | 10/2005 | Odrich et al. | |
| 6,951,462 B2 | 10/2005 | Kumar et al. | |
| 6,955,258 B2 | 10/2005 | Howlett et al. | |
| 7,172,071 B2 * | 2/2007 | Hawkins | A61F 2/4601 |
| | | | 206/438 |
| 7,198,150 B1 * | 4/2007 | Blaschke | A61F 2/0095 |
| | | | 206/221 |
| 7,207,801 B2 | 4/2007 | Vogt et al. | |
| 7,451,870 B2 | 11/2008 | Donahoe et al. | |
| 7,594,577 B2 * | 9/2009 | Iwatschenko | A61B 17/8847 |
| | | | 206/438 |
| 7,748,526 B2 * | 7/2010 | Iwatschenko | A61O 5/062 |
| | | | 206/219 |
| 7,770,722 B2 | 8/2010 | Donahoe et al. | |
| 7,780,448 B2 | 8/2010 | Kim | |
| 7,887,327 B2 | 2/2011 | Marotta | |
| 8,042,684 B2 | 10/2011 | Guenter et al. | |
| 8,070,491 B2 | 12/2011 | Mundwiler et al. | |
| 8,303,307 B2 | 11/2012 | Mundwiler et al. | |
| 8,425,227 B2 | 4/2013 | Marotta | |
| 8,486,501 B2 | 7/2013 | Manabe et al. | |
| 8,584,838 B2 * | 11/2013 | Cheetham | A61O 5/064 |
| | | | 206/219 |
| 8,637,128 B2 | 1/2014 | Jemelin | |
| 8,695,800 B2 | 4/2014 | Kaczorowski et al. | |
| 8,790,408 B2 | 7/2014 | Marotta | |
| 8,827,702 B2 | 9/2014 | Mamraev | |
| 8,864,494 B2 | 10/2014 | Guenter et al. | |
| 2004/0095844 A1 * | 5/2004 | Miller | A61L 24/06 |
| | | | 366/130 |
| 2004/0112781 A1 | 6/2004 | Hofverberg et al. | |
| 2007/0298379 A1 | 12/2007 | D'Alise | |
| 2011/0244029 A1 * | 10/2011 | Barenholz | A61K 9/127 |
| | | | 424/450 |

FOREIGN PATENT DOCUMENTS

| | | |
|---|---|---|
| EP | 1087719 | 2/2003 |
| EP | 1523955 | 4/2005 |
| EP | 1749501 | 2/2007 |
| EP | 1970025 | 9/2008 |
| EP | 2567672 | 3/2013 |
| EP | 2335639 | 4/2014 |
| TW | I400184 | 7/2013 |
| WO | 9965416 | 12/1999 |
| WO | 02098744 | 12/2002 |
| WO | 03059190 | 7/2003 |
| WO | 2005039434 | 5/2005 |
| WO | 2009045013 | 4/2009 |
| WO | 2011012284 | 2/2011 |
| WO | 2011012287 | 2/2011 |

* cited by examiner

IMPLANT CARRIER, MIXING POT, AND IMPLANT CARRIER ASSEMBLY

BACKGROUND

Technical Field

The disclosure relates to an implant carrier and a mixing pot and particularly relates to an implant carrier assembly.

Description of Related Art

Due to factors such as the increasing national income, the aging population structure, and introduction of new medical technology, the public have increasing demand for health care services, which leads to growth of the health-related industries, especially in the field of medical implantation, such as dental and bone implants.

As people age, the joints, bones, and teeth of the bodies will gradually degenerate and cause inconvenience in daily life. In such cases, it is required to implant artificial substitutes or fixtures, such as artificial teeth, artificial joints, and artificial bone nails, to replace or fix the degenerating joints, bones, or teeth so as to maintain their functions. Therefore, the development of medical implants in areas, such as the compatibility and affinity of medical implants to biological cells, is drawing more and more attention.

According to the current dental implant process, in order to prevent surface contamination or damage caused by the user who touches the implant when moving the implant, a special container is usually prepared for containing the implant. Besides, a mixture containing growth factor is usually applied to the surface of the implant, after the implant is taken out of the container, for enhancing the bonding between the implant and human tissue. However, this process may increase the risk of inadvertent touch and contamination if not handled properly.

SUMMARY

The disclosure provides an implant carrier assembly, which mixes powder and a liquid in a mixing pot by an assembly structure between the mixing pot and an implant carrier, and the mixture is able to flow into a space where an implant is located.

In an embodiment of the disclosure, an implant carrier assembly is provided, which includes a first housing, a second housing, a mixing pot, and a sealed container. The second housing is openably assembled to the first housing to form a receiving space. An implant is adapted to be disposed in the receiving space. The second housing has a hole communicating with the receiving space. The mixing pot is for receiving powder. The sealed container receives a liquid therein. The sealed container is adapted to be inserted into the mixing pot, and the mixing pot is adapted to be assembled to the second housing, such that the sealed container is aligned with the hole. During assembly of the mixing pot and the second housing, the second housing compresses the sealed container toward the mixing pot and breaks the sealed container, such that the liquid flows from the sealed container into the mixing pot to mix with the powder, and a mixture thereof flows into the receiving space through the hole and applied to a surface of the implant.

In an embodiment of the disclosure, an implant carrier is provided, which includes a first housing, a second housing, and a cover. The second housing is openably assembled to the first housing to form a receiving space. An implant is adapted to be disposed in the receiving space. The second housing has a hole communicating with the receiving space. The cover is detachably assembled to the second housing to seal or open the hole. When the cover is detached from the second housing, a mixture containing a growth factor is adapted to enter the receiving space through the hole to be applied to the implant.

In an embodiment of the disclosure, a mixing pot is provided, which includes a pot body having a receiving chamber, an opening, and a tip. Powder is adapted to be stored in the receiving chamber. The tip is disposed on an inner bottom wall of the receiving chamber at a position away from the opening, and the tip faces the opening. A sealed container storing a liquid is adapted to be inserted into the receiving chamber through the opening and pierced by the tip, such that the liquid flows from the sealed container into the receiving chamber to be mixed with the powder.

In an embodiment of the disclosure, the sealed container is a liposome storing pure water, and the powder includes a growth factor.

In an embodiment of the disclosure, the second housing includes a protrusion and a first thread around the protrusion, and the hole is located at a center of the protrusion. The mixing pot includes a second thread to be engaged with the first thread to assemble the mixing pot to the second housing, such that the protrusion compresses the sealed container toward the inner bottom wall of the mixing pot.

In an embodiment of the disclosure, the mixing pot includes a tip disposed on the inner bottom wall. During assembly of the mixing pot and the second housing, the second housing compresses the sealed container toward the inner bottom wall of the mixing pot, such that the tip pierces the sealed container.

In an embodiment of the disclosure, the first housing includes a groove and a holding part disposed upright in the groove, and the implant is adapted to be detachably engaged with the holding part.

In an embodiment of the disclosure, the second housing includes a column, a top part, and a connection part, wherein the top part and the connection part extend in the same direction from two opposite sides of the column. The connection part is assembled to a bottom of the groove, such that the column and the top part seal the groove. The hole is located on the column on a side opposite to the groove.

In an embodiment of the disclosure, the second housing is flexible, and a notch exists between the connection part and the column for the column and the top part to rotate with respect to the connection part to open or close the groove.

In an embodiment of the disclosure, the first housing and the second housing form a polygonal column when assembled to each other, and the top part and the bottom of the groove respectively form a column face of the polygonal column.

In an embodiment of the disclosure, the cover includes a recess receiving an accessory.

In an embodiment of the disclosure, the pot body includes a locking thread on an outer side at a position adjacent to the opening. The pot body is adapted to be locked to another container by the locking thread, so a mixture of the liquid and the powder is able to flow into the another container.

Based on the aforementioned embodiments, the implant is received in the implant carrier, and when the implant is to be used, the cover is removed from the implant carrier and the implant carrier is assembled with the mixing pot to form the implant carrier assembly. The sealed container storing the liquid is partially inserted into the mixing pot and broken as being compressed during the assembly of the mixing pot and the implant carrier, such that the liquid flows out of the sealed container to mix with the powder sufficiently to form the mixture, and then the mixture flows into the inner space through the hole of the implant carrier to be applied to the implant. Accordingly, in the mixing and applying processes before use, as described above, the user does not need to directly contact the mixture and the implant. Therefore, the risk of the implant being contaminated by the outside is reduced effectively to meet the requirement of clinical use.

To make the aforementioned and other features and advantages of the disclosure more comprehensible, several embodiments accompanied with figures are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
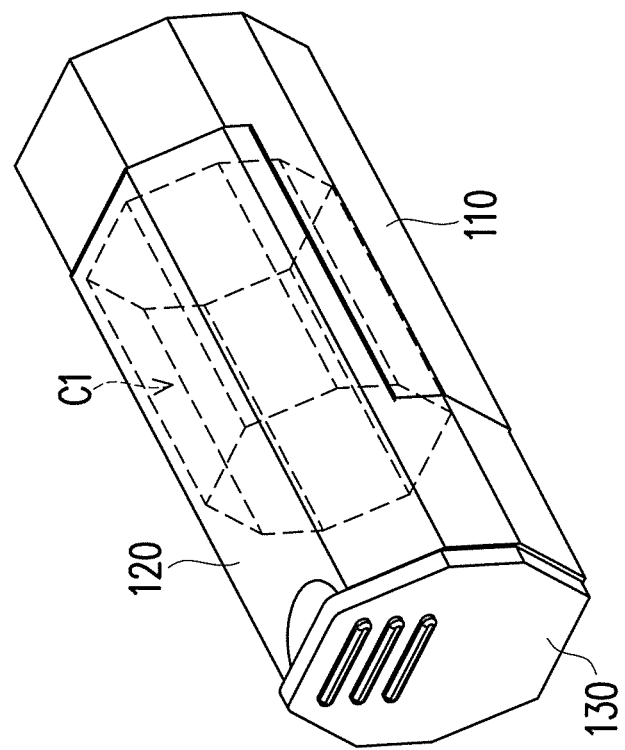
FIG. 1 is a schematic diagram showing an implant caller according to an embodiment of the disclosure.
Figure 2:
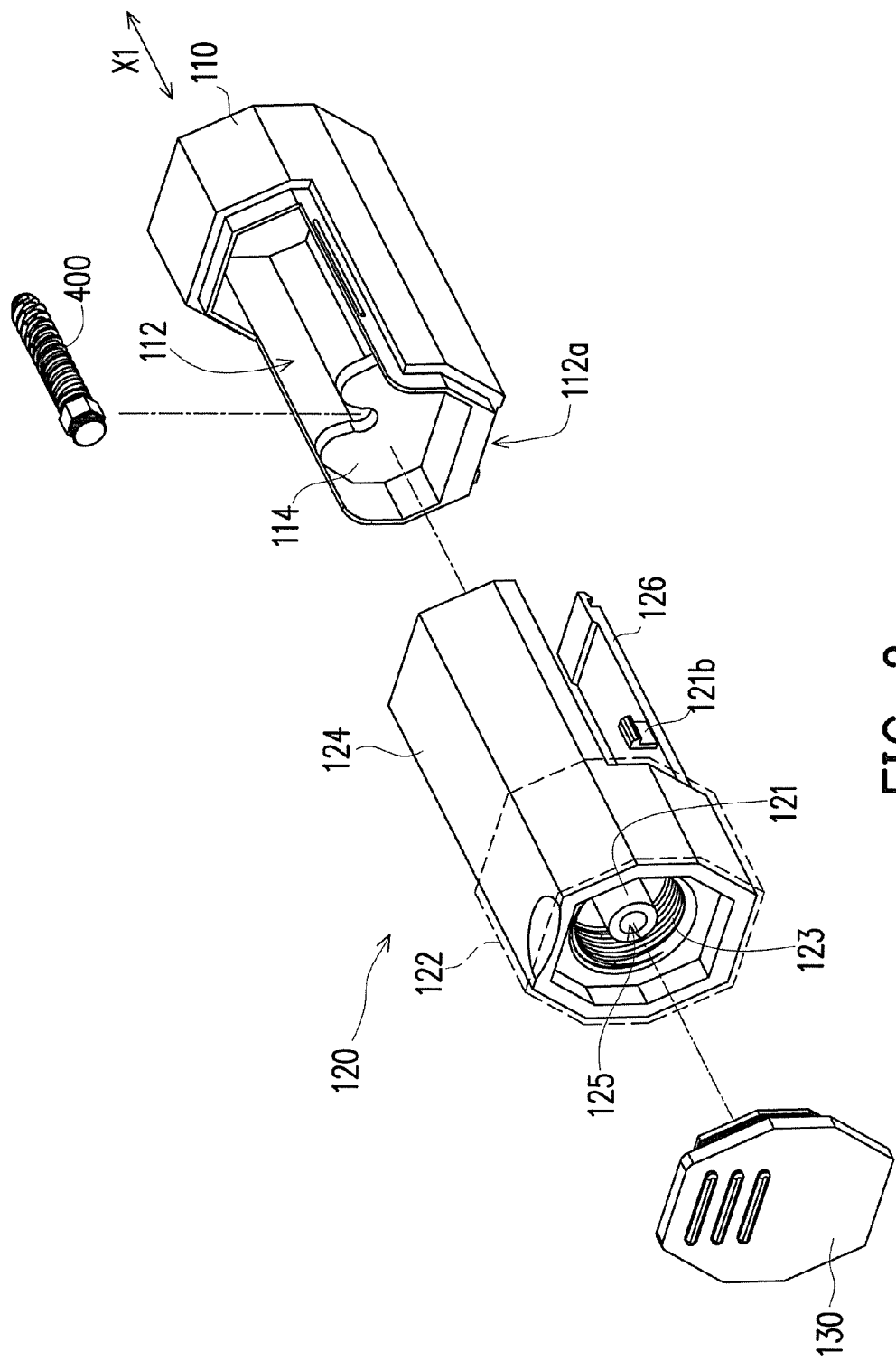
FIG. 2 and FIG. 3 respectively show the implant carrier of FIG. 1 from different aspects.
Figure 3:
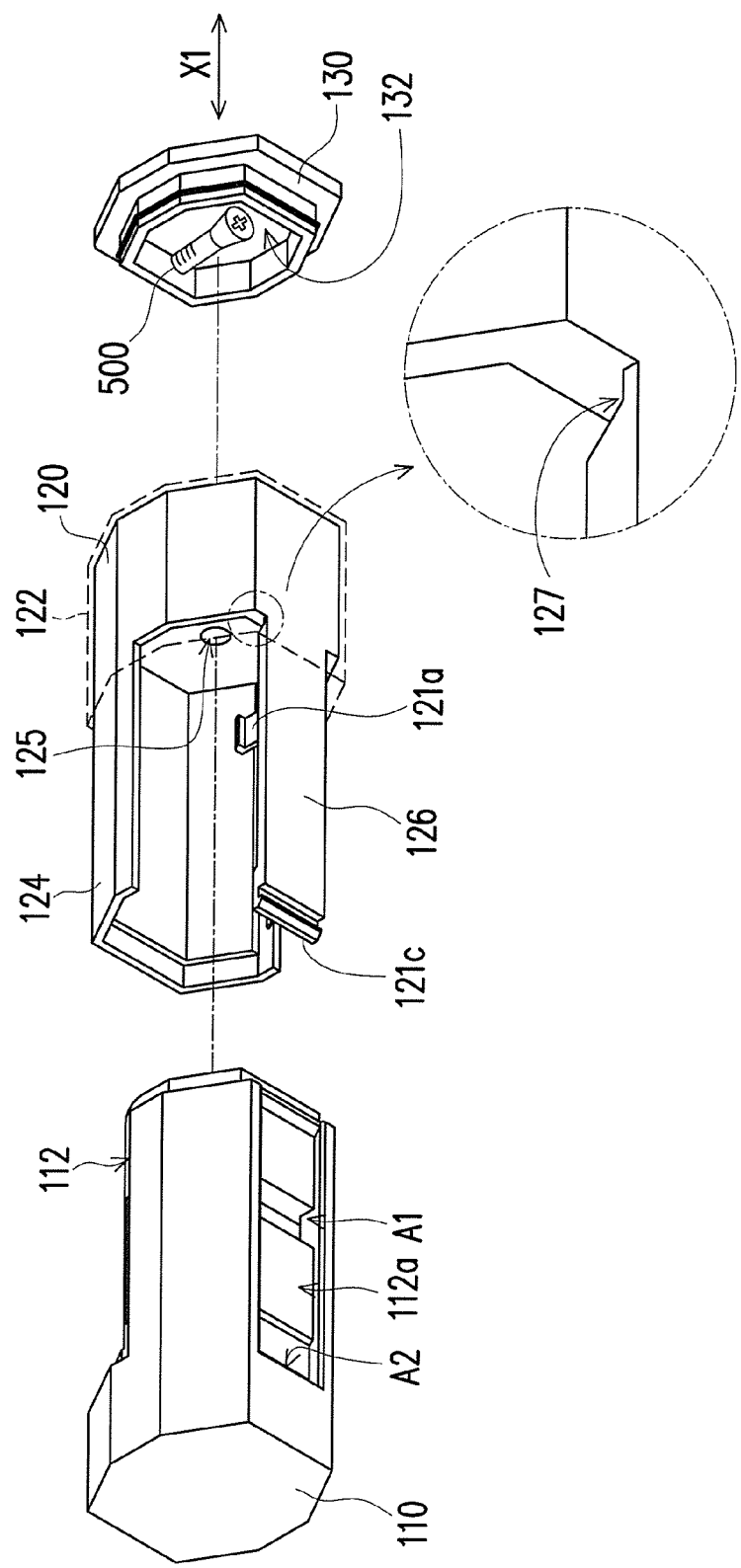

FIG. 1 is a schematic diagram showing an implant carrier according to an embodiment of the disclosure. FIG. 2 and FIG. 3 respectively show the implant carrier of FIG. 1 from different aspects. In this embodiment, an implant carrier 100 includes a first housing 110, a second housing 120, and a cover 130. The first housing 110 and the second housing 120 are openably assembled to each other to form a receiving space C1 when in a closed state (as indicated by the broken lines here). The receiving space C1 receives an implant 400 therein and exposes the implant 400 when the first housing 110 and the second housing 120 are in an opened state for the user to retrieve the implant 400. The opened/closed states will be described in detail later.

With reference to FIG. 2 and FIG. 3, in this embodiment, the first housing 110 has a groove 112 and a holding part 114 disposed upright in the groove 112. The implant 400 is a tooth root bone implant (but not limited thereto), for example, and is adapted to be detachably engaged with the holding part 114. As shown in FIG. 2, the implant 400 has a hexagonal contour to be engaged with a concave of the holding part 114, such that the implant 400 is suspended in the groove 112 and extends along an axis X1, so as to minimize the area of contact between the implant 400 and the carrier structure, thereby reducing the risk of external contamination and inadvertent touch.

Moreover, the second housing 120 has a column 122, a top part 124, and a connection part 126, wherein the top part 124 and the connection part 126 extend in the same direction from two opposite sides of the column 122. The connection part 126 is assembled to a bottom of the groove 112, such that the column 122 and the top part 124 seal the groove 112. Specifically, as shown in FIG. 3, the connection part 126 has a strip structure, and the second housing 120 further has a plurality of hooks 121a, 121b, and 121c disposed on the connection part 126. Correspondingly, the groove 112 has a slot 112a at the bottom, wherein the connection part 126 is inserted into the slot 112a with the hooks 121a, 121b, and 121c hooked therein. As shown in FIG. 2 and FIG. 3, the hooks 121a and 121b are hooked on a recess A1 while the hook 121c is hooked on a recess A2, so as to assemble the second housing 120 to the first housing 110 through the connection part 126.

Figure 4:
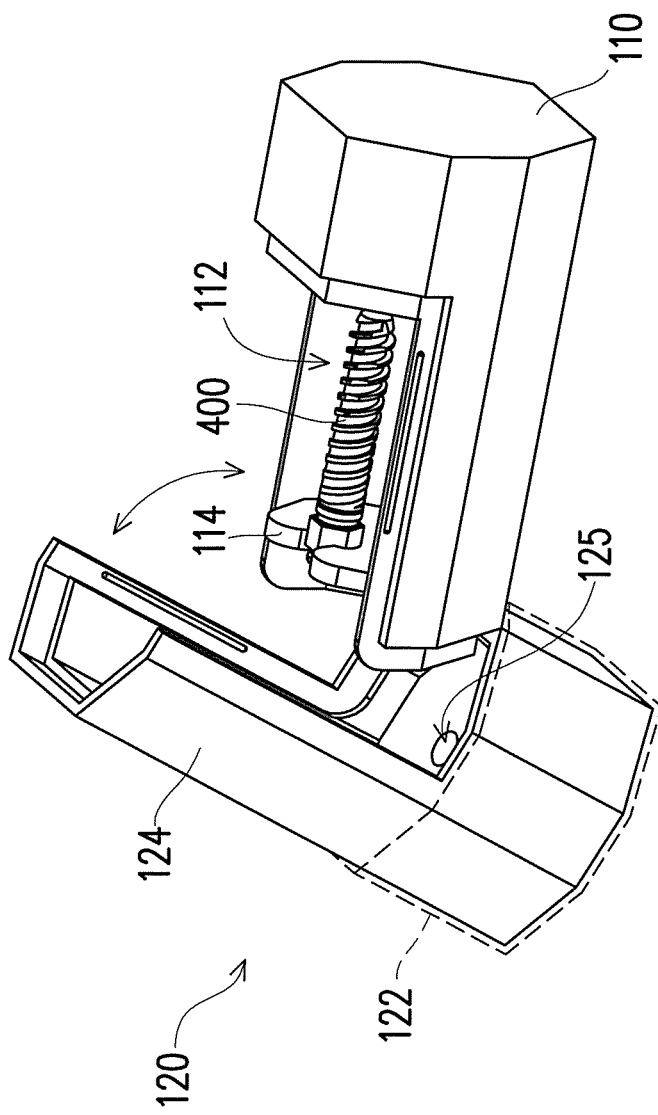
FIG. 4 is a schematic diagram showing another state of the implant carrier of FIG. 1.

FIG. 4 is a schematic diagram showing another state of the implant carrier of FIG. 1. With reference to FIG. 3 and FIG. 4, the second housing 120 is made of a high molecular polymer, for example, and is therefore flexible. It should be noted that the second housing 120 further has a notch 127 (as shown in FIG. 3) formed between the connection part 126 and the column 122. The notch 127 is a thin wall formed between the connection part 126 and the column 122 when the second housing 120 is molded, for example, for the column 122 and the top part 124 to rotate (turn) with respect to the connection part 126, such that the user can move and open the second housing 120 by force to expose the groove 112 of the first housing 110, thereby taking out or putting in the implant 400.

Moreover, in this embodiment, the cover 130 has a recess 132 for receiving an accessory 500, such as a healing screw, to serve as an auxiliary member of the implant 400.

It should also be noted that, as shown in FIG. 1 and FIG. 4, the first housing 110 and the second housing 120 form a polygonal column after being assembled to each other. The top part 124 and the bottom of the groove 112 respectively form a column face of the polygonal column, so as to prevent the implant carrier 100 from rolling when in use and increase the structural stability.

Figure 5:
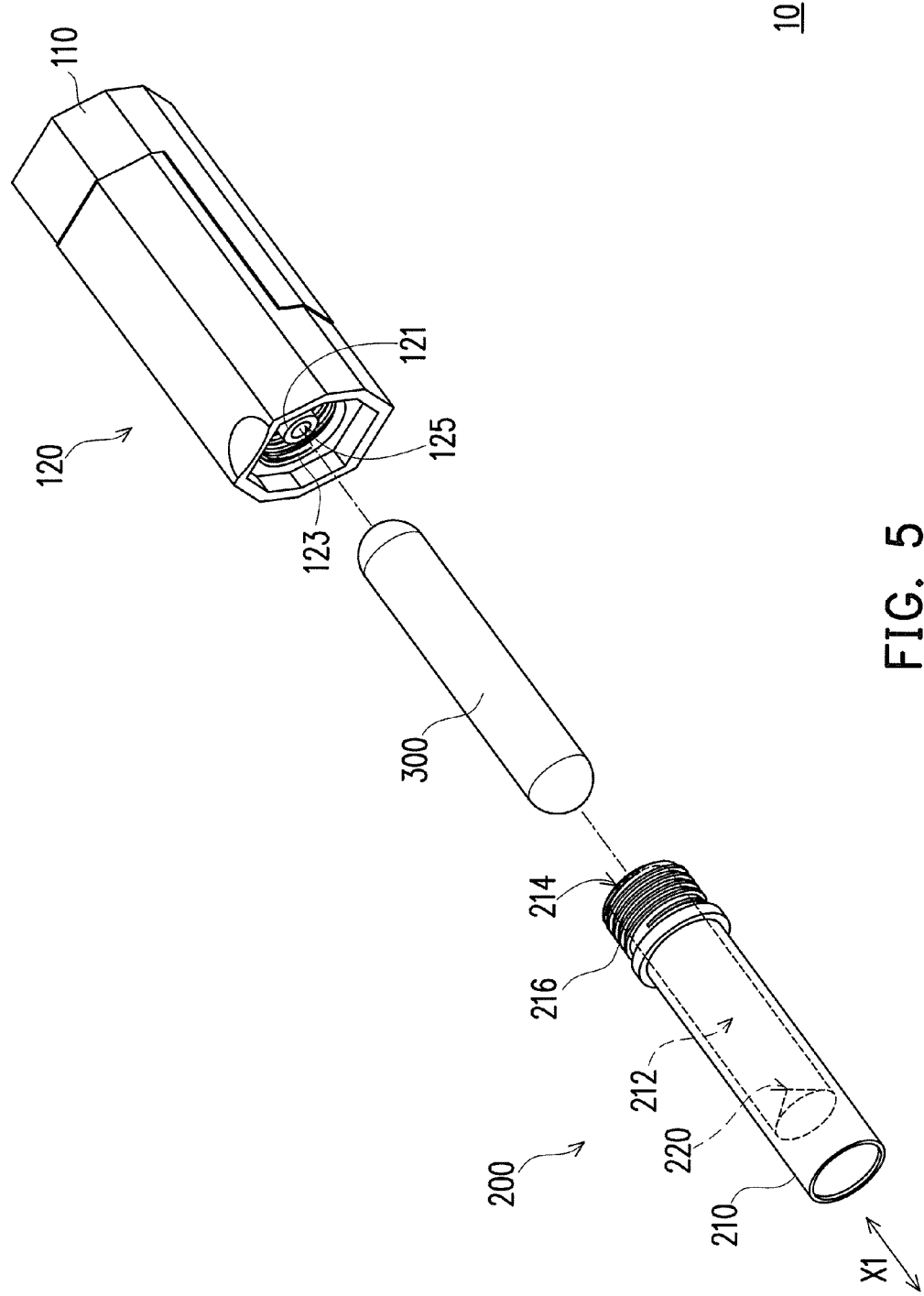
FIG. 5 is an exploded diagram showing an implant carrier assembly according to an embodiment of the disclosure.

FIG. 5 is an exploded diagram showing an implant carrier assembly according to an embodiment of the disclosure. With reference to FIG. 2, FIG. 4, and FIG. 5, in this embodiment, an implant carrier assembly 10 includes a mixing pot 200, a sealed container 300, and a part of the aforementioned implant carrier 100, wherein the mixing pot 200 stores powder (not shown) that contains a growth factor (e.g. BMP-2), and the sealed container 300 is a pure water liposome, for example, which stores a liquid (not shown), such as pure water, therein. As described above, when a mixture containing the growth factor is to be applied to the surface of the implant 400, the assembly structure and processes of this embodiment eliminate the risk of contamination during the mixing or applying process.

Specifically, the mixing pot 200 includes a pot body 210 and a tip 220 disposed therein, wherein the pot body 210 has a receiving chamber 212 and an opening 214. The powder containing the growth factor is adapted to be stored in the receiving chamber 212. The tip 220 is disposed on an inner bottom wall of the receiving chamber 212 at a position away from the opening 214. The tip 220 faces the opening 214. In addition, the mixing pot 200 further has a thread 216 on the outer side at a position close to the opening 214.

Correspondingly, the second housing 120 has a protrusion 121 and a thread 123 formed on the column 122 on a side opposite to the groove 112 of the first housing 110. That is, when the column 122 and the top part 124 are closed on the groove 112 of the first housing 110, the protrusion 121 and the thread 123 are still on the outer side of the structure. In other words, the protrusion 121 extends away from the groove 112 and the thread 123 is formed around the protrusion 121, and the cover 130 is detachably assembled to the column 122 of the second housing 120 to shield or expose the protrusion 121 and the thread 123 on the column 122. It is important to note that the second housing 120 further has a hole 125 located at the center of the protrusion 121, wherein the hole 125 penetrates the column 122 along the axis X1 to communicate with the receiving space C1 (i.e. the groove 112 of the first housing 110 closed by the second housing 120) and is exposed when the cover 130 is removed from the second housing 120.

As shown in FIG. 5, when the sealed container 300 storing the liquid is inserted into the receiving chamber 212 through the opening 214, the user then aligns the opening 214 of the mixing pot 200 with the second housing 120 with the cover 130 removed to assemble them. That is, the threads 123 and 216 are engaged with each other to assemble the mixing pot 200 to the column 122 of the second housing 120, so as to form the implant carrier assembly 10. It should be noted that, in the assembly process, the protrusion 121 compresses the sealed container 300 and squeezes the sealed container 300 into the receiving chamber 212 of the mixing pot 200. Accordingly, when the sealed container 300 comes in contact with the tip 220 of the inner bottom wall, due to the material of the sealed container 300 (liposome), the sealed container 300 is pierced by the tip 220 and the liquid (pure water) therein flows into the receiving chamber 212 of the mixing pot 200 to mix with the powder in the receiving chamber 212. Then, the user shakes the assembly of the mixing pot 200 and the implant carrier 100 to sufficiently mix the powder and the liquid. Next, the mixture of the powder and the liquid flows into the receiving space C1 through the hole 125 of the second housing 120 to be applied sufficiently on the implant 400. In the processes of assembly and mixing, the user is not required to touch the implant 400 or the mixture directly. That is, the processes are completed in the space formed by the mixing pot 200 and the implant carrier 100. Therefore, the risk of contamination is reduced effectively.

To sum up, in the aforementioned embodiments of the disclosure, the implant is received in the implant carrier before use, so as to avoid contact with the outside. When the implant is to be used, the assembly structure of the mixing pot, the sealed container, and the implant carrier allows the growth factor to be applied to the surface of the implant, so as to improve the effectiveness of early osseointegration after implantation into the human body.

In other words, by removing the cover from the implant carrier and assembling the implant carrier with the mixing pot and the sealed container to form the implant carrier assembly, the sealed container storing the liquid is partially inserted into the mixing pot and broken as being compressed during the assembly of the mixing pot and the implant carrier, such that the liquid flows out of the sealed container to mix with the powder sufficiently to form the mixture, and then the mixture flows into the inner space through the hole of the implant carrier to be applied to the implant. Accordingly, in the mixing and applying processes before use, as described above, the user does not need to directly contact the mixture and the implant. Therefore, the risk of the implant being contaminated by the outside is reduced effectively to meet the requirement of clinical use.

Further, the outer shape of the implant carrier is a polygonal column, which helps to stabilize the structure and prevents rolling.

It will be apparent to those skilled in the art that various modifications and variations can be made to the disclosed embodiments without departing from the scope or spirit of the disclosure. In view of the foregoing, it is intended that the disclosure covers modifications and variations of this disclosure provided that they fall within the scope of the following claims and their equivalents.

What is claimed is:

1. An implant carrier assembly, comprising:
   a first housing;
   a second housing openably assembled to the first housing to form a receiving space, wherein an implant is disposed in the receiving space and the second housing comprises a hole communicating with the receiving space;
   a mixing pot for receiving a powder; and
   a sealed container for receiving a liquid, wherein in an assembly process, the sealed container is inserted into the mixing pot and the mixing pot is assembled to the second housing such that the sealed container is aligned with the hole, and the sealed container is compressed and squeezed by the second housing and the mixing pot to be broken, such that the liquid flows from the sealed container into the mixing pot to mix with the powder, and a mixture of the liquid and the powder flows into the receiving space through the hole to be applied to a surface of the implant.

2. The implant carrier assembly according to claim 1, further comprising:
   a cover detachably assembled to the second housing to seal or open the hole.

3. The implant carrier assembly according to claim 1, wherein the sealed container is a liposome storing pure water, and the powder comprises a growth factor.

4. The implant carrier assembly according to claim 1, wherein the second housing comprises a protrusion and a first thread around the protrusion, wherein the hole is located at a center of the protrusion, and the mixing pot comprises a second thread to be engaged with the first thread to assemble the mixing pot to the second housing, such that the protrusion compresses the sealed container toward an inner bottom wall of the mixing pot.

5. The implant carrier assembly according to claim 4, wherein the mixing pot comprises a tip disposed on the inner bottom wall, and during assembly of the mixing pot and the second housing, the second housing compresses the sealed container toward the inner bottom wall of the mixing pot, such that the tip pierces the sealed container.

6. The implant carrier assembly according to claim 1, the first housing comprises a groove and a holding part disposed upright in the groove, and the implant is detachably engaged with the holding part, wherein the second housing comprises a column, a top part, and a connection part, wherein the top part and the connection part extend in the same direction from two opposite sides of the column, and the connection part is assembled to a bottom of the groove, such that the column and the top part seal the groove, and the hole is located on the column on a side opposite to the groove.

7. The implant carrier assembly according to claim 6, wherein the second housing is flexible, and a notch exists between the connection part and the column for the column and the top part to rotate with respect to the connection part to open or close the groove.

8. The implant carrier assembly according to claim 6, wherein the first housing and the second housing form a polygonal column when assembled to each other, and the top part and the bottom of the groove respectively form a column face of the polygonal column.

9. An implant carrier, comprising:
   a first housing;
   a second housing assembled to the first housing to form a receiving space, wherein an implant is disposed in the receiving space and the second housing comprises a hole communicating with the receiving space; and
   a cover detachably assembled to the second housing to seal or open the hole, wherein when the cover is detached from the second housing, a mixture is adapted to enter the receiving space through the hole to be applied to the implant.

10. The implant carrier according to claim 9, wherein the cover comprises a recess receiving an accessory.

11. The implant carrier according to claim 9, wherein the first housing comprises a groove and a holding part disposed upright in the groove, and the implant is detachably engaged with the holding part.

12. The implant carrier according to claim 11, wherein the second housing comprises a column, a top part, and a connection part, wherein the top part and the connection part extend in the same direction from two opposite sides of the column, and the connection part is assembled to a bottom of the groove, such that the column and the top part seal the groove, and the hole is located on the column on a side opposite to the groove.

13. The implant carrier according to claim 12, wherein the second housing is flexible, and a notch exists between the connection part and the column for the column and the top part to rotate with respect to the connection part to open or close the groove.

14. The implant carrier according to claim 12, wherein the first housing and the second housing form a polygonal column when assembled to each other, and the top part and the bottom of the groove respectively form a column face of the polygonal column.

15. The implant carrier according to claim 9, wherein the mixture comprising a growth factor.

16. A mixing pot for receiving a powder, the mixing pot comprising:
   a pot body comprising a receiving chamber and an opening, wherein the powder is stored in the receiving chamber; and
   a tip disposed on an inner bottom wall of the receiving chamber at a position away from the opening and facing the opening, wherein a sealed container storing a liquid is inserted into the receiving chamber through the opening and pierced by the tip, such that the liquid flows from the sealed container into the receiving chamber to be mixed with the powder, wherein the pot body comprises a thread on an outer side at a position adjacent to the opening, and the pot body is locked to another container by the thread, so a mixture of the liquid and the powder is able to flow into the another container.

17. The mixing pot according to claim 16, wherein the sealed container storing the liquid is a pure water liposome, and the powder comprises a growth factor.

* * * * *